United States Patent
Kishimoto (10) Patent No.: US 10,231,869 B2
(45) Date of Patent: Mar. 19, 2019

(54) INTRAOCULAR SURGERY SYSTEM

(71) Applicant: SENJU PHARMACEUTICAL CO., LTD., Osaka-shi, Osaka (JP)

(72) Inventor: Makoto Kishimoto, Moriyama (JP)

(73) Assignees: SENJU PHARMACEUTICAL CO., LTD., Osaka (JP); KISHIMOTO, MAKOTO, Shiga (JP)

( * ) Notice: Subject to any disclaimer, the term of this patent is extended or adjusted under 35 U.S.C. 154(b) by 73 days.

(21) Appl. No.: 15/305,906

(22) PCT Filed: Feb. 27, 2015

(86) PCT No.: PCT/JP2015/056003
§ 371 (c)(1),
(2) Date: Oct. 21, 2016

(87) PCT Pub. No.: WO2015/163006
PCT Pub. Date: Oct. 29, 2015

(65) Prior Publication Data
US 2017/0042731 A1    Feb. 16, 2017

(30) Foreign Application Priority Data

Apr. 23, 2014 (JP) ................... 2014-089684

(51) Int. Cl.
*A61M 1/00* (2006.01)
*A61F 9/007* (2006.01)

(52) U.S. Cl.
CPC .......... *A61F 9/00745* (2013.01); *A61F 9/007* (2013.01); *A61M 1/0076* (2013.01);
(Continued)

(58) Field of Classification Search
CPC .............. A61F 9/00736; A61F 9/00745; A61F 9/0076; A61M 1/0076
See application file for complete search history.

(56) References Cited

U.S. PATENT DOCUMENTS 3,774,613 A   11/1973  Woods, Jr. et al.
4,790,818 A   12/1988  DeLuca et al.
(Continued)

FOREIGN PATENT DOCUMENTS

JP  48-078798 A   10/1973
JP  09-313496 A   12/1997
JP  2004-305682 A   11/2004

OTHER PUBLICATIONS

International Search Report dated Apr. 20, 2015, issued in counterpart International Application No. PCT/JP2015/056003.

*Primary Examiner* — Bhisma Mehta
*Assistant Examiner* — Matthew A Engel
(74) *Attorney, Agent, or Firm* — Westerman, Hattori, Daniels & Adrian, LLP (57) ABSTRACT

The present invention is an intraocular surgery system using a Venturi pump and capable of preventing clogging due to nucleus fragments, despite a reduced aspiration flow rate. The intraocular surgery system includes: an air pumping means (21); a Venturi tube (22) to which air is supplied from the air pumping means; a drainage tank (28) that is connected to a narrowed part of the Venturi tube; an intraocular surgery device (1) configured to fragment a nucleus inside an eye using ultrasonic vibrations, and discharge the nucleus together with a perfusate; a first aspiration tube (31) through which the perfusate discharged from the intraocular surgery device passes; a separation device (4) to which the first aspiration tube is connected, and that is configured to separate the nucleus from the perfusate that has flown from the first aspiration tube; and a second aspiration tube (32) that has an inner diameter that is smaller than an inner diameter of the first aspiration tube, and is configured to supply the drainage tank with the perfusate discharged from the separation device.

6 Claims, 5 Drawing Sheets

(52) U.S. Cl.
CPC ........ *A61B 2218/007* (2013.01); *A61M 1/008* (2013.01); *A61M 2205/7536* (2013.01); *A61M 2210/0612* (2013.01)

(56) References Cited

U.S. PATENT DOCUMENTS

| | | | | |
|---|---|---|---|---|
| 5,354,268 A * | 10/1994 | Peterson | ............. | A61M 1/0031 604/319 |
| 5,487,725 A * | 1/1996 | Peyman | ............. | A61F 9/00727 604/22 |
| 5,733,256 A * | 3/1998 | Costin | ................ | A61F 9/00745 604/22 |
| 6,117,150 A * | 9/2000 | Pingleton | ............... | A61B 17/00 604/35 |
| 6,217,584 B1 * | 4/2001 | Nun | ....................... | A61B 17/16 128/898 |
| 6,328,747 B1 * | 12/2001 | Nun | ....................... | A61B 17/16 604/22 |
| 6,375,635 B1 * | 4/2002 | Moutafis | ............ | A61B 17/3203 604/22 |
| 7,172,601 B2 * | 2/2007 | Ben-Nun | ............... | A61B 18/02 606/107 |
| 2002/0013572 A1 * | 1/2002 | Berlin | ....................... | A61F 2/14 606/4 |
| 2003/0158567 A1 * | 8/2003 | Ben-Nun | ............... | A61B 18/02 606/167 |
| 2004/0082939 A1 * | 4/2004 | Berlin | ....................... | A61F 2/14 606/5 |
| 2008/0108934 A1 * | 5/2008 | Berlin | ....................... | A61F 2/14 604/8 |
| 2008/0114300 A1 * | 5/2008 | Muri | ................... | A61M 1/0058 604/131 |
| 2008/0294095 A1 * | 11/2008 | Zacharias | ........... | A61M 1/0031 604/65 |
| 2010/0030134 A1 * | 2/2010 | Fitzgerald | ........... | A61M 1/0031 604/34 |
| 2013/0060210 A1 * | 3/2013 | Ross | ................... | A61M 1/0035 604/318 |
| 2014/0276364 A1 * | 9/2014 | Sussman | ............. | A61F 9/00745 604/22 |
| 2015/0080783 A1 * | 3/2015 | Berlin | ................. | A61F 9/00781 604/8 |
| 2015/0297407 A1 * | 10/2015 | Saimovici | ........... | A61F 9/00754 606/107 |
| 2015/0359666 A1 * | 12/2015 | Zacharias | ........... | A61F 9/00736 604/500 |
| 2016/0128869 A1 * | 5/2016 | Zacharias | ........... | A61F 9/00736 604/22 |

* cited by examiner

INTRAOCULAR SURGERY SYSTEM

TECHNICAL FIELD

The present invention relates to an intraocular surgery system, and a separation device that is used for the same.

BACKGROUND ART

In recent years, in order to cure an eye disease such as a cataract, a surgical operation in which the crystalline lens within an eye is replaced with an intraocular lens (an artificial crystalline lens) is often adopted. As an example of the aforementioned surgical operation, phacoemulsification and aspiration (PEA), in which the crystalline lens in the diseased part is fragmented using ultrasonic vibration and the emulsified crystalline lens is aspirated, is commonly used. In this surgical operation, an ultrasonic handpiece (hereinafter simply referred to as "the handpiece" as well), which is an ultrasonic emulsification and aspiration device, is used. The handpiece includes a rod-shaped main body, which is supported by the operator's hand. A transducer that generates ultrasonic vibrations, and a horn that amplifies the ultrasonic vibrations generated by the transducer, are built into the main body. A fragmentation tip for fragmenting and emulsifying a crystalline lens is attached to a front end of the main body. The tube-shaped fragmentation tip is coupled to the horn, and is able to provide ultrasonic vibrations to the crystalline lens that is to be subjected to the surgical operation.

In the surgical operation, the crystalline lens is fragmented by ultrasonic vibrations while a perfusate is supplied into the anterior chamber of the eye. The crystalline lens is emulsified by ultrasonic vibrations, and is discharged to the outside together with the perfusate, via an aspiration channel provided in the handpiece. However, part of the nucleus of the crystalline lens is discharged as fragments (nucleus fragments), together with the perfusate.

CITATION LIST

Patent Literature

Patent Literature 1: JP 2004-305682A

SUMMARY OF INVENTION

Usually, a peristaltic pump or a Venturi pump is used to aspirate the perfusate discharged from the handpiece. Peristaltic pumps have an advantage in that the aspiration pressure and the aspiration flow rate of the perfusate can be independently controlled. However, peristaltic pumps are expensive, which is problematic. In contrast, Venturi pumps are cheap because of their simple structure. However, Venturi pumps have a problem in that the aspiration pressure and the aspiration flow rate cannot be independently controlled. Specifically, the aspiration pressure and the aspiration flow rate are set to be proportional to each other. Therefore, there is a problem in which, for example, if the aspiration pressure is set to a value that is sufficient for reliably aspirating the nucleus fragment of the crystalline lens, the aspiration flow rate will be too high. Here, in order to reduce the aspiration flow rate without lowering the aspiration pressure, it can be conceived of reducing the diameter of the aspiration tube between the handpiece and the Venturi pump. However, with such a configuration, there is the risk of the nucleus fragments clogging the aspiration tube.

The present invention has been made to solve the above-described problems, and aims to provide an intraocular surgery system that is a simple system using a Venturi pump, but is capable of preventing clogging due to nucleus fragments, despite a reduced aspiration flow rate, and a separation device used in the system.

The intraocular surgery system according to one aspect of the present invention includes: an air pumping means; a Venturi tube to which air is supplied from the air pumping means; a drainage tank that is connected to a narrowed part of the Venturi tube; an intraocular surgery device configured to fragment a nucleus inside an eye using ultrasonic vibrations, and discharge the nucleus together with a perfusate; a first aspiration tube through which the perfusate discharged from the intraocular surgery device passes; a separation device to which the first aspiration tube is connected, and is configured to separate the nucleus from the perfusate that has flown from the first aspiration tube; and a second aspiration tube that has an inner diameter that is smaller than an inner diameter of the first aspiration tube, and is configured to supply the drainage tank with the perfusate discharged from the separation device. The separation device includes: a main body having an inner space; a discharge part that is in communication with an upper end portion of the inner space and to which the second aspiration tube is connected; and an aspiration part that is in communication with the inner space at a position lower than the discharge part, and to which the first aspiration tube is connected.

With this configuration, a so-called Venturi pump, which includes an air pumping means and a Venturi tube, is used to aspirate the perfusate from the intraocular surgery device to the drainage tank. Therefore, it is easy to aspirate the perfusate. The first aspiration tube, the separation device, and the second aspiration tube are disposed between the intraocular surgery device and the drainage tank. Since the inner diameter of the second aspiration tube is smaller than the inner diameter of the first aspiration tube, it is possible to reduce the aspiration flow rate of the perfusate. On the other hand, since the inner diameter of the first aspiration tube is large, the nucleus fragments of the crystalline lens can be aspirated from the intraocular surgery device to the separation device without clogging the first aspiration tube. The separation device includes: a main body having an inner space; a discharge part that is in communication with an upper end portion of the inner space and to which the second aspiration tube is connected; and an aspiration part that is in communication with the inner space at a position lower than the discharge part, and to which the first aspiration tube is connected. With this configuration, the discharge part is located at a position that is higher than the aspiration part, and therefore it is possible to prevent the nucleus fragments aspirated from the aspiration part to the inner space from being discharged from the discharge part. Therefore, the nucleus fragments are prevented from flowing into the second aspiration tube that has a small inner diameter.

With the above-described configuration, it is possible to reduce the aspiration flow rate of perfusate despite using a Venturi pump, and it is also possible to prevent clogging due to nucleus fragments of the crystalline lens.

In the above-described intraocular surgery system, the discharge part may be attached to an upper end portion of the main body. With this configuration, it is possible to more reliably prevent the nucleus fragments of the crystalline lens aspirated from the aspiration part from being discharged from the discharge part.

In the above-described intraocular surgery system, the aspiration part may be configured to extend downward at an angle that is smaller than 90 degrees with respect to the vertical direction. With this configuration, the nucleus fragments of the crystalline lens aspirated from the aspiration part travel downward in the inner space of the main body. Therefore, it is possible to more reliably prevent the nucleus fragments from being discharged from the discharge part.

In the above-described intraocular surgery system, the inner space may be formed in a tube shape having an axis that extends in the vertical direction, and the aspiration part may be provided along a direction of a tangent to an outer circumferential surface of the inner space.

In the above-described intraocular surgery system, in order to prevent clogging due to the nucleus fragments of the crystalline lens, the first aspiration tube may have an inner diameter that is within a range of 0.9 mm to 3.0 mm, for example.

The above-described intraocular surgery system may further include an adjustment mechanism that is configured to adjust the inner diameter of the second aspiration tube. With this configuration, it is possible to freely adjust the aspiration flow rate of the perfusate.

A separation device according to one aspect of the present invention is a separation device that is to be connected between a first aspiration tube and a second aspiration tube of an intraocular surgery system that includes: an air pumping means; a Venturi tube to which air is supplied from the air pumping means; a drainage tank that is connected to a narrowed part of the Venturi tube; an intraocular surgery device configured to fragment a nucleus inside an eye using ultrasonic vibrations, and discharge the nucleus together with a perfusate; the first aspiration tube through which the perfusate discharged from the intraocular surgery device passes; the second aspiration tube that has an inner diameter that is smaller than an inner diameter of the first aspiration tube, and is connected to the drainage tank. The separation device includes: a main body having an inner space; a discharge part that is in communication with the inner space and to which the second aspiration tube is to be connected; and an aspiration part that is in communication with the inner space at a position lower than the discharge port, and to which the first aspiration tube is to be connected.

The system according to one aspect of the present invention is a simple system using a Venturi pump, but is capable of preventing clogging due to nucleus fragments, despite a reduced aspiration flow rate.

BRIEF DESCRIPTION OF DRAWINGS

Each of FIGS. 5A to 5H is a front view showing another form of the separation device.

Each of FIGS. 8A and 8B is a photograph showing the aspiration of pieces of cheese performed by an example of the present invention.

DESCRIPTION OF EMBODIMENTS

Figure 1:
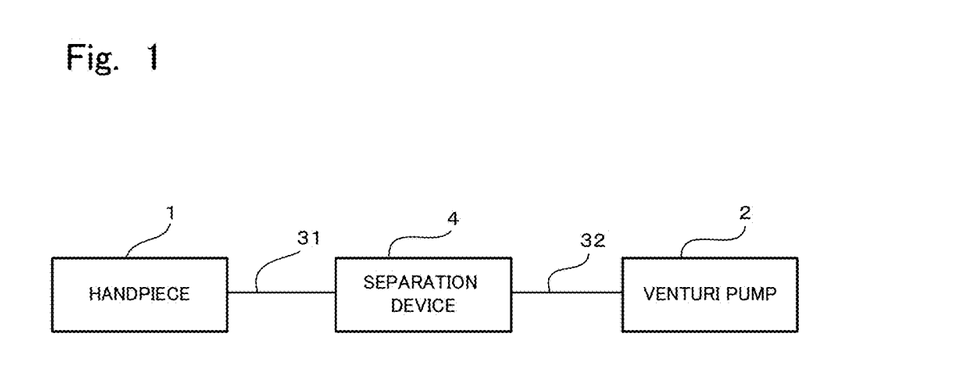
FIG. 1 is a block diagram showing an embodiment of an intraocular surgery system according to the present invention.

The following describes an embodiment of an intraocular surgery system according to the present invention with reference to the drawings. As shown in FIG. 1, this system includes a handpiece 1 that fragments the crystalline lens, and a Venturi pump 2 is used to aspirate the perfusate from the handpiece 1. Two aspiration tubes 31 and 32 and a separation device 4 are disposed between the handpiece 1 and the Venturi pump 2. The following describes the configuration of the intraocular surgery system in detail.

1. Handpiece

Figure 2:
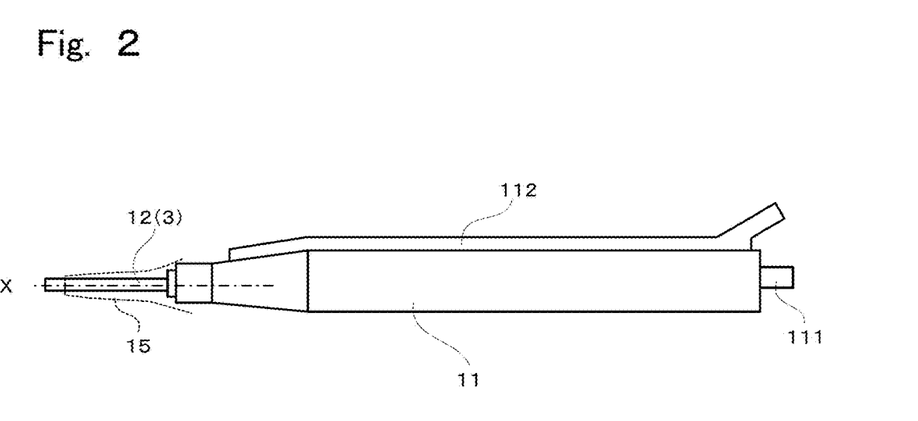
FIG. 2 is a side view of a handpiece included in the system shown in FIG. 1.

FIG. 2 is a side view of the handpiece. As shown in the drawing, the handpiece 1 according to the present embodiment is formed in a cylindrical shape, and includes a main body 11 that is to be held in the operator's hand. A transducer (not shown) that generates ultrasonic vibrations, and a horn (not shown) that amplifies the ultrasonic vibrations generated by the transducer, are built into the main body 11. A tube-shaped fragmentation tip 12 for fragmenting and emulsifying the crystalline lens is attached to a front end of the main body 11, and a cylindrical sleeve 15 made of a flexible material such as silicon is disposed so as to enclose the fragmentation tip 12. The sleeve 15 is provided in order to prevent parts of the fragmentation tip 12 other than its front end from coming into contact with the diseased part, and the fragmentation tip 12 slightly protrudes from the front end of the sleeve 15. The fragmentation tip 12 is coupled to the horn inside the main body 11, and is able to provide ultrasonic vibrations to the crystalline lens that is to be subjected to the surgical operation.

The fragmentation tip 12 is vibrated so as to rotate back and forth around the axis of the tube (around an axis X described below). For example, the fragmentation tip 12 is vibrated so as to rotate 30,000 to 40,000 times a minute by a rotational angle of 2 to 4 degrees. An outer circumferential surface of the main body 11 is provided with a perfusate supply channel 112 that extends toward the front end of the main body 11, so that the perfusate can be supplied from near the fragmentation tip 12 to the anterior chamber inside the eye. Since the fragmentation tip 12 has a tube shape, the fragmented crystalline lens can be aspirated therein together with the perfusate. The aspirated crystalline lens, together with the perfusate, passes through an aspiration channel that is built into the main body 11, and is discharged to the outside from a port 111 that is at a rear end of the main body 11. A first aspiration tube 31 is connected to the port 111, and the crystalline lens and perfusate are discharged therefrom. The fragmentation tip is not particularly limited to any form. The fragmentation tip may rotate to fragment the crystalline lens as described above, or move back and forth to fragment the crystalline lens.

2. Venturi Pump

Figure 3:
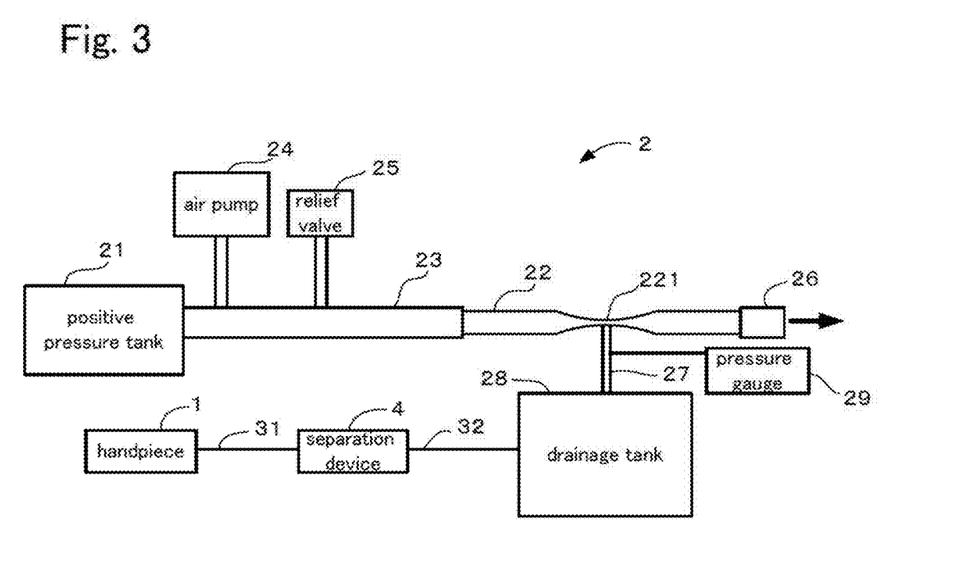
FIG. 3 is a schematic configuration diagram showing a Venturi pump included in the system shown in FIG. 1.

FIG. 3 is a schematic configuration diagram for the Venturi pump. As shown in the drawing, the Venturi pump 2 according to the present embodiment includes a positive pressure tank 21, a Venturi tube 22, and a connector tube 23 that connects them. Air flows from the positive pressure tank 21 to the Venturi tube 22 via the connector tube 23. An air pump 24 and a relief valve 25 are coupled to the connector tube 23 from the upstream side. A silencer 26 is attached to a downstream end portion of the Venturi tube 22.

With the above-described configuration, air from the positive pressure tank 21 is pumped to the Venturi tube 22 upon the air pump 24 being driven. Air that has passed through the Venturi tube 22 is discharged while being silenced by the silencer 26. If the pressure of air passing through the connector tube 23 exceeds a predetermined value, air is relieved to the outside via the relief valve 25.

A coupling tube 27 is attached to a narrowed part 221 of the Venturi tube 22, and the coupling tube 27 is coupled to a drainage tank 28. The drainage tank 28 is a tank that retains the perfusate that has been discharged from the above-described handpiece 1. As described above, airflows to the Venturi tube 22 upon the air pump 24 being driven, and consequently the drainage tank 28, which is in communication with the narrowed part 221 of the Venturi tube 22, has negative pressure. As a result, the perfusate discharged from the handpiece 1 is aspirated and flows into the drainage tank 28.

A pressure gauge 29 is attached to the coupling tube 27, and measures the pressure in the coupling tube 27. With this configuration, it is possible to measure the aspiration pressure of perfusate. Furthermore, although not shown in the drawings, the Venturi pump 2 is provided with a controller, and it is possible to adjust the output from the air pump 24. With this configuration, for example, it is possible to adjust the output from the air pump 24 and adjust the aspiration pressure according to the pressure measured by the pressure gauge 29.

The configuration between the drainage tank 28 and the handpiece 1 is as follows. The first aspiration tube 31 that is connected to the handpiece 1 is connected to the separation device 4 described below, and the second aspiration tube 32 that is connected to the separation device 4 is connected to the drainage tank 28. Here, as described below, the inner diameter of the first aspiration tube 31 is preferably within the range of 0.9 mm to 3.0 mm, for example, so that the nucleus that is aspirated by the handpiece 1 can pass through the first aspiration tube 31. It is further preferable that the inner diameter is within the range of 1.0 mm to 2.0 mm, and it is particularly preferable that the inner diameter is within the range of 1.0 mm to 1.75 mm. The inner diameter of the second aspiration tube 32 is smaller than the inner diameter of the first aspiration tube 31, and is preferably within the range of 0.05 mm to 2.0 mm, for example. It is further preferable that the inner diameter of the second aspiration tube 32 is within the range of 0.1 mm to 2.0 mm.

2. Separation Device

Figure 4:
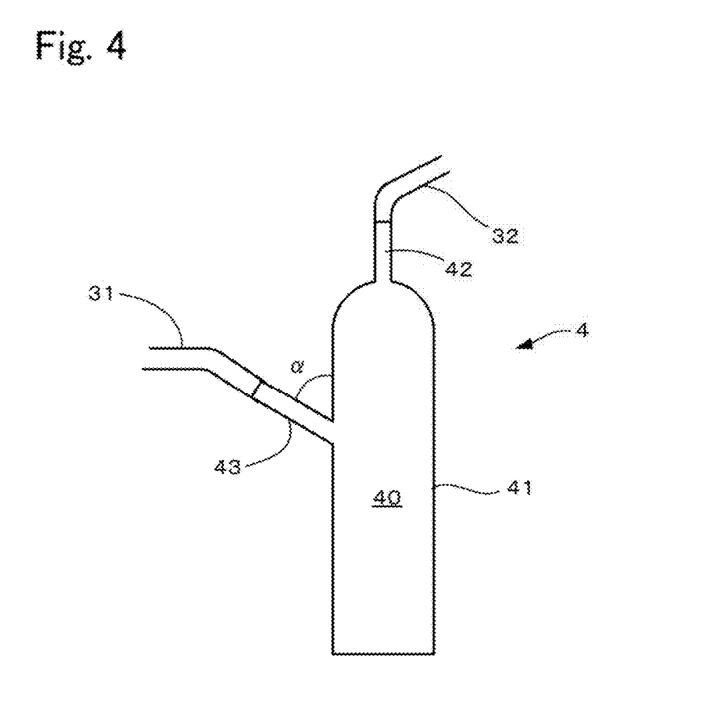
FIG. 4 is a front view showing a separation device included in the system shown in FIG. 1.

FIG. 4 is a front view of the separation device. As shown in the drawing, the separation device 4 includes: a main body 41 that is cylindrical; a discharge part 42 that is provided on the upper end of the main body 41; and an aspiration part 43 that is provided on a side surface of the main body 41, which are integrated as one piece. The main body 41 has a lower end portion that is configured as a flat bottom surface, and an upper end portion that has a hemispherical shape that projects upward. An inner space 40 that is closed is formed by the members other than the discharge part 42 and the aspiration part 43 described above. The discharge part 42 has a tube shape that projects upward from the upper end of the main body 41, and is in communication with the inner space 40 of the main body 41 and with the outside. The aspiration part 43 is formed in a tube shape, and is connected to the outer circumferential surface of the main body 41 at an angle α so as to be inclined downward. The aspiration part 43 is in communication with the inner space 40 of the main body 41 and with the outside.

The separation device 4 may be made of glass, plastic, or the like. Although the color of the separation device 4 is not particularly limited, it is preferable that the separation device 4 is transparent so that the inner space 40 can be seen from the outside.

3. Cataract Surgery Using Intraocular Surgery System

Next, a description is given of a method for performing a cataract surgery using the intraocular surgery system configured as described above. A cataract surgery mainly includes the following four steps: (1) making an incision in the anterior capsule; (2) emulsifying and aspirating the crystalline lens; (3) aspirating the cortex; and (4) inserting an intraocular lens. The following mainly describes steps 1 and 2. First, in step 1, an incision is made in the anterior capsule while the shape of the anterior chamber is maintained using a viscoelastic material or the like. Next, in step 2, an incision layer is formed in the cornea and the sclera, the fragmentation tip 12 is inserted into the anterior chamber, and the crystalline lens is fragmented and emulsified by the vibration of the fragmentation tip 12. The crystalline lens that has been emulsified is aspirated from the opening in the front end of the fragmentation tip 12 together with the perfusate, and is discharged to the outside from the port 111 via the discharge channel in the handpiece. The anterior chamber is maintained in a stable state by balancing the inflow and the outflow of perfusate at this time.

Before the operation is performed in the above-described manner, the air pump 24 is driven so that air is pumped to the Venturi tube 22. As a result, air is aspirated from the inside of the drainage tank 28 toward the Venturi tube 22 via the coupling tube 27 that is coupled to the narrowed part 221 of the Venturi tube 22, and the inside of the drainage tank 28 has negative pressure. As a result, the perfusate that has been discharged from the port 111 of the handpiece 1 flows into the drainage tank 28 via the first aspiration tube 31, the separation device 4, and the second aspiration tube 32.

During this process, part of the nucleus of the crystalline lens that has been fragmented by the fragmentation tip 12 is discharged as fragments (hereinafter referred to as "nucleus fragments") to the outside from the port 111 together with the perfusate. The nucleus fragments travel toward the separation device 4, passing through the first aspiration tube 31. Since the first aspiration tube 31 has an inner diameter that is approximately larger than the nucleus fragments, the nucleus fragments flow into the separation device 4 without clogging the first aspiration tube 31.

The first aspiration tube 31 is connected to the aspiration part 43 of the separation device 4. Therefore, the nucleus fragments, together with the perfusate, flow from the aspiration part 43 of the separation device 4 to the inner space 40 of the separation device 4. Here, the aspiration part 43 is connected to the main body 41 of the separation device 4 so as to be inclined downward relative to the surface of the main body 41. Therefore, the nucleus fragments flow downward into the main body 41. Since the specific gravity of the nucleus fragments is greater than that of the perfusate, the nucleus fragments sink downward in the inner space 40 of the main body 41, and accumulate at the bottom part of the inner space 40. Meanwhile, the perfusate is discharged from the discharge part 42 that is connected to an upper part of the main body 41, and flows into the drainage tank 28 via the second aspiration tube 32. Thus, the nucleus fragments fragmented by the handpiece 1 are stored in the separation device 4, and are prevented from flowing further downstream, i.e., to the second aspiration tube 32.

4. Features

As described above, in the present embodiment, the perfusate is aspirated from the handpiece 1 to the drainage tank 28, using a so-called Venturi pump. Therefore, it is easy to aspirate the perfusate. Consequently, it is possible to reduce the cost of the system. Also, the first aspiration tube 31, the separation device 4, and the second aspiration tube 32 are disposed between the handpiece 1 and the drainage tank 28, and the inner diameter of the second aspiration tube 32 is smaller than the inner diameter of the first aspiration tube 31. Therefore, it is possible to reduce the aspiration flow rate of perfusate. On the other hand, since the inner diameter of the first aspiration tube 31 is large, the nucleus fragments of the crystalline lens can be aspirated from the handpiece 1 to the separation device 4 without clogging the first aspiration tube 31. In the separation device 4, the discharge part 42 is located at a position that is higher than the aspiration part 43. Therefore, the nucleus fragments that have been aspirated from the aspiration part 43 to the inner space 40 are prevented from being discharged from the discharge part 42 to the second aspiration tube 32. Therefore, the nucleus fragments are prevented from flowing into the second aspiration tube 32 that has a small inner diameter.

As described above, with the system according to the present embodiment, it is possible to reduce the aspiration flow rate of perfusate despite using a Venturi pump, and it is also possible to prevent clogging due to nucleus fragments of the crystalline lens. In addition, since the Venturi pump has a simple configuration, it is possible to downsize the whole system. Therefore, it is easy to carry the intraocular surgery system around, and it is possible to perform a cataract operation at various locations.

5. Modifications

Although an embodiment of the present invention has been described above, the present invention is not limited to the above-described embodiment, and may be variously modified without departing from the spirit of the invention.

For example, the separation device 4 is not limited to the above-described form, and various forms may be adopted. Specifically, in the separation device 4, although it is preferable that the discharge part 42 is disposed at or in the vicinity of the upper end portion of the main body 41, any configuration may be adopted insofar as the discharge part 42 is disposed at a position that is higher than the aspiration part 43. Therefore, the following forms as shown in FIG. 5A to 5H are possible.

Figure 5A:
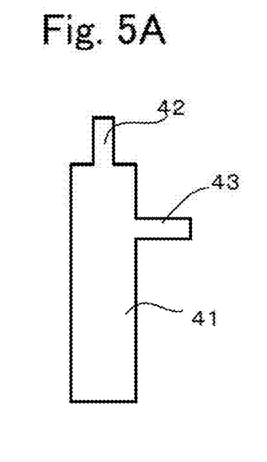

(1) The aspiration part is only required to be coupled to the main body so as to be horizontal or inclined downward toward the outer circumferential surface of the main body (FIG. 5A).

Figure 5B:
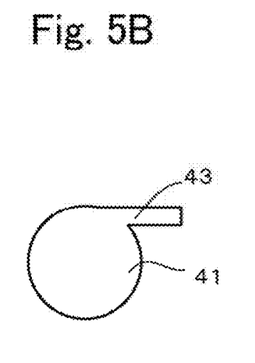

(2) If the aspiration part is coupled to the main body in the direction of the tangent to the outer circumferential surface of the main body, the nucleus fragments spirally travel downward in the inner space of the main body due to centrifugal force (FIG. 5B: cross-sectional view). Therefore, the nucleus fragments reliably sink downward in the main body.

Figure 5C:
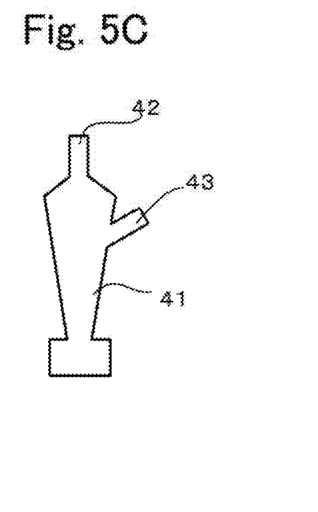
Figure 5D:
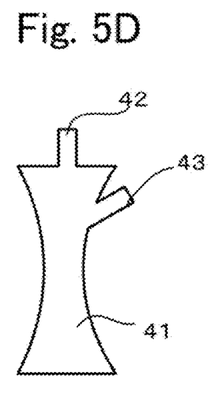
Figures 5E, 5F:
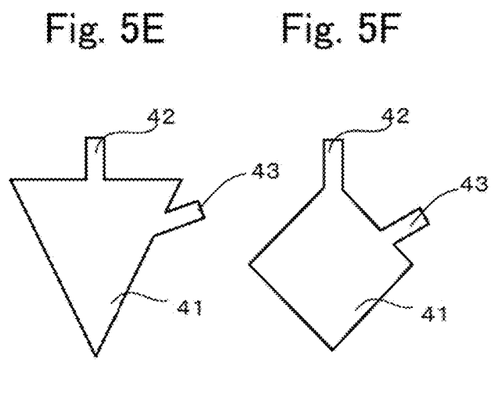
Figure 5G:
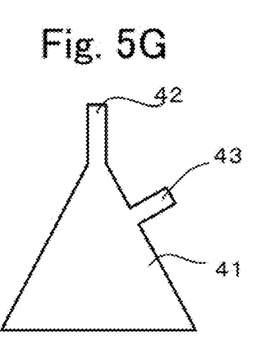
Figure 5H:
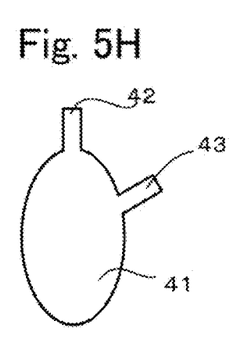

(3) It is possible that the outer circumferential surface of the main body is formed such that the diameter thereof decreases in the downward direction, and a storage portion that has a large diameter is provided at a lower end portion of the main body (FIG. 5C). With this configuration, once nucleus fragments have sunk downward and have entered the storage portion, the nucleus fragments are unlikely to travel upward because the diameter of the opening in an upper end of the storage portion is small. Similarly, an hourglass shape as shown in FIG. 5D may be adopted.

(4) The main body is not particularly limited to any form, and various forms may be adopted. For example, a cylindrical shape, a polygonal column shape, a triangular shape in front view, a circular shape in front view, an elliptical shape in front view, and an inverted triangular shape in front view may be adopted (FIGS. 5E to 5H).

In the above-described embodiment, the inner diameter of the second aspiration tube 32 is constant. However, it is also possible to change the inner diameter of the second aspiration tube 32 by pinching the second aspiration tube 32 using a pinch cock or a pinch valve. Thus, it is possible to adjust the aspiration flow rate. Note that in order to change the inner diameter of the second aspiration tube 32, adjustment mechanisms other than a pinch cock and a pinch valve may be used insofar as the mechanisms are able to change the inner diameter by pressing the second aspiration tube 32 from the outside.

Figure 6:
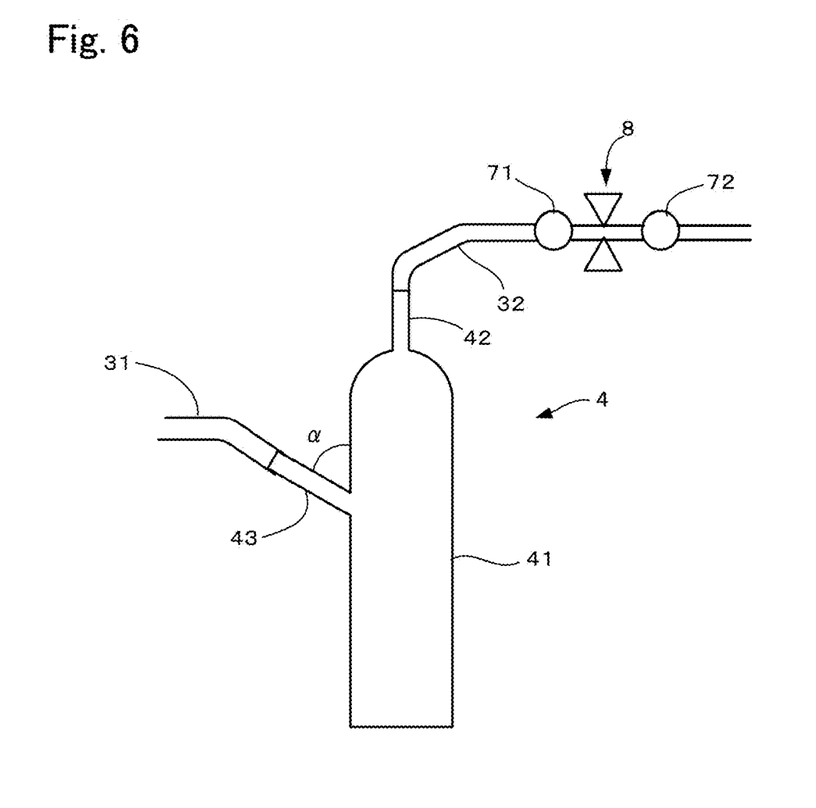
FIG. 6 is a partial schematic diagram showing another example of the system shown in FIG. 1.
Figure 7:
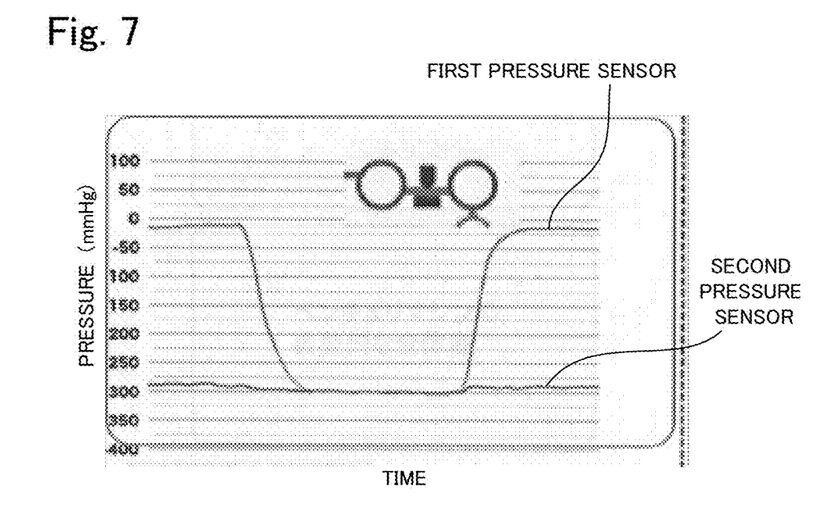
FIG. 7 is a graph showing changes in the pressure in the system shown in FIG. 5.

It is also possible to provide pressure sensors respectively at positions that are upstream and downstream of an adjustment mechanism as described above. With this configuration, it is possible to detect that the fragmentation tip 12 of the handpiece 1 has been clogged by nucleus fragments of the crystalline lens. In the following description, as shown in FIG. 6, a pressure sensor on the Venturi pump side with respect to an adjustment mechanism 8 is referred to as a first pressure sensor 71, and a pressure sensor on the separation device 4 side with respect to the adjustment mechanism 8 is referred to as a second pressure sensor 72. With this configuration, before the fragmentation tip 12 is closed, the pressure detected by the first pressure sensor 71 is higher while the second aspiration tube 32 is pressed by the adjustment mechanism 8, as shown in FIG. 7. However, since the pressure in the entire fragmentation tip 12 increases due to the nucleus fragments, the pressure detected by the second pressure sensor 72 decreases, and consequently the pressures detected by the pressure sensors 71 and 72 become the same. Thus, it is possible to detect that the fragmentation tip 12 is clogged by the nucleus fragments.

The Venturi pump is not particularly limited to any form insofar as the Venturi pump is provided with a Venturi tube and the drainage tank is allowed to have a negative pressure due to the narrowed part and the drainage tank being coupled to each other. Also, although air is pumped using a positive pressure tank and an air pump in the above-described Venturi pump, the Venturi pump is not particularly limited insofar as air can be pumped.

Working Examples

The following describes a working example of the present invention. However, the present invention is not limited to the following working example.

In this working example, a perfusate was aspirated using the intraocular surgery system shown in FIGS. 1 to 4. The system was set as follows.

The aspiration pressure of the Venturi pump: 300 mmHg (negative pressure)
The inner diameter of the first aspiration tube: 1.75 mm
The inner diameter of the second aspiration tube: 0.1 mm The inner diameter of the separation device: 10 mm
The height of the separation device: 80 mm
The position of the discharge part of the separation device: on the upper end of the main body
The position of the aspiration part of the separation device: at a height of 40 mm from the bottom surface of the main body
The angle α of the aspiration part of the separation device: 60 degrees Although the aspiration pressure was 300 mmHg as specified above, the aspiration flow rate was 40 ml/min (measured using the first aspiration tube 31 shown in FIG. 1) because the inner diameter of the second aspiration tube that is located on the Venturi pump side with respect to the separation device is small. Therefore, despite using the Venturi pump, it is possible to reduce the aspiration flow rate while maintaining the aspiration pressure.

Figure 8A:
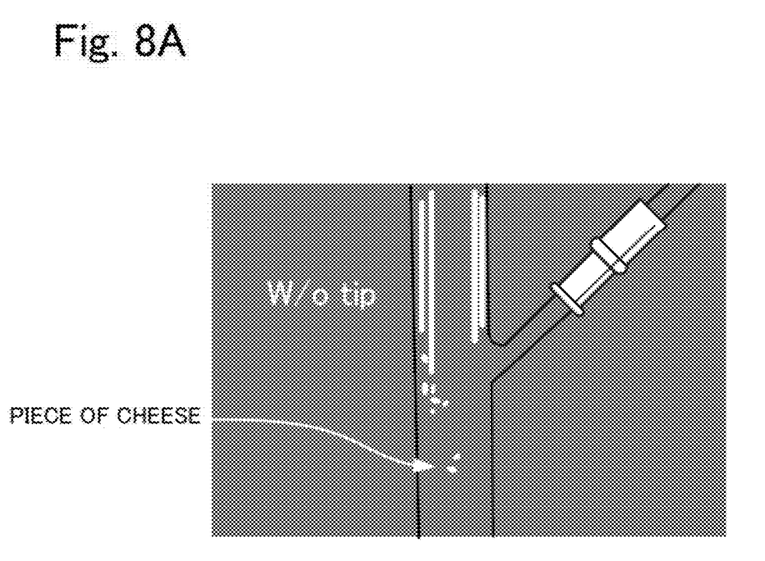
Figure 8B:
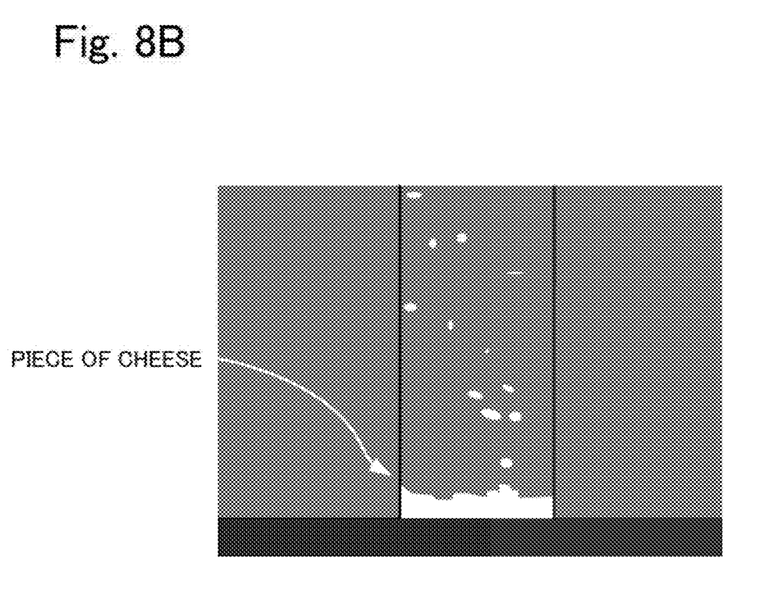

In the above-described system, a large number of pieces of cheese having a diameter of approximately 0.9 mm were fed from the first aspiration tube toward the separation device as simulated nucleus fragments. As a result, as shown in FIGS. 8A and 8B, the pieces of cheese gradually accumulated on the bottom part of the separation device without clogging the first aspiration tube.

REFERENCE SIGNS LIST

1 Handpiece (Intraocular surgery device)
21 Positive pressure tank (Air pumping means)
22 Venturi tube
221 Narrowed part
24 Air pump (Air pumping means)
28 Drainage tank
31 First aspiration tube
32 Second aspiration tube
4 Separation device
41 Main body
42 Discharge part
43 Aspiration part

The invention claimed is:
1. An intraocular surgery system comprising:
an air pumping means;
a Venturi tube to which air is supplied from the air pumping means;
a drainage tank that is connected to a narrowed part of the Venturi tube;
an intraocular surgery device configured to fragment a nucleus inside an eye using ultrasonic vibrations, and discharge the nucleus together with a perfusate;
a first aspiration tube through which the perfusate discharged from the intraocular surgery device passes;
a separation device to which the first aspiration tube is connected, and that is configured to separate the nucleus from the perfusate that has passed from the first aspiration tube, and configured to discharge the perfusate; and
a second aspiration tube that has an inner diameter that is smaller than an inner diameter of the first aspiration tube, and is configured to supply the drainage tank with the perfusate discharged from the separation device,
wherein the separation device includes:
a main body having an inner space;
a discharge part that is in communication with the inner space and to which the second aspiration tube is connected; and
an aspiration part that is in communication with the inner space at a position lower than the discharge part, and to which the first aspiration tube is connected.

2. The intraocular surgery system according to claim 1, wherein the discharge part is provided on an upper end portion of the main body.

3. The intraocular surgery system according to claim 1, wherein the aspiration part extends downward at an angle that is smaller than 90 degrees with respect to a vertical direction.

4. The intraocular surgery system according to claim 1,
wherein the inner space is formed in a tube shape having an axis that extends in a vertical direction, and
the aspiration part is provided along a direction of a tangent to an outer circumferential surface of the inner space.

5. The intraocular surgery system according to claim 1, wherein the inner diameter of the first aspiration tube is within a range of 0.9 mm to 3.0 mm.

6. The intraocular surgery system according to claim 1, further comprising an adjustment mechanism that is configured to adjust the inner diameter of the second aspiration tube.

* * * * *